United States Patent
Muller et al.

(10) Patent No.: US 7,133,490 B2
(45) Date of Patent: Nov. 7, 2006

(54) RADIOLOGICAL IMAGING DEVICE, METHOD AND PROGRAM OF CONTROL ASSOCIATED WITH THE DEVICE

(75) Inventors: Serge Muller, Guyancourt (FR); Luc Miotti, Vanves (FR); Jean-Pierre Saladin, Bagneux (FR)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 253 days.

(21) Appl. No.: 09/825,910

(22) Filed: Apr. 4, 2001

(65) Prior Publication Data

US 2001/0038679 A1    Nov. 8, 2001

(30) Foreign Application Priority Data

Apr. 26, 2000  (FR) .................................. 00 05311

(51) Int. Cl.
*A61B 6/04* (2006.01)

(52) U.S. Cl. .......................................... 378/37; 378/62

(58) Field of Classification Search .................. 378/37, 378/62

See application file for complete search history.

(56) References Cited

U.S. PATENT DOCUMENTS

| 5,133,020 A | 7/1992 | Giger et al. .................... 382/6 |
| 5,539,797 A | 7/1996 | Heidsieck et al. ............ 378/37 |

FOREIGN PATENT DOCUMENTS

| EP | 1004275 | 5/2000 |
| FR | 2648589 | 12/1990 |

*Primary Examiner*—Edward J. Glick
*Assistant Examiner*—Jurie Yun
(74) *Attorney, Agent, or Firm*—Cantor Colburn LLP

(57) ABSTRACT

Radiological imaging device comprising an emitter of an X-ray beam and a receiver of the X-ray beam after it has crossed an organ, the organ being capable of being placed between the receiver and a compression element, capable of being removably fixed on the device. A calculation unit includes a means for optimizing the image quality over a particular area defined by the compression element.

15 Claims, 8 Drawing Sheets

FIG_3

FIG_6

FIG_7

FIG_8

RADIOLOGICAL IMAGING DEVICE, METHOD AND PROGRAM OF CONTROL ASSOCIATED WITH THE DEVICE

CROSS-REFERENCE TO RELATED APPLICATIONS

This applications claims the benefit of a priority under 35 USC 119 to French Patent Application No. 0005311 filed Apr. 26, 2000, the entire subject matter contents which are hereby incorporated by reference.

BACKGROUND OF THE INVENTION

The present invention belongs to the field of radiology intended for study of object in particular of the human body in general and of certain organs in particular, such as the breasts, the heart, the circulatory system, etc.

As is standard, a radiology device comprises an X-ray tube capable of emitting an X-ray beam along a given axis, an X-ray receiver placed on the path of the X-ray beam, the organ to be studied being interposed between the X-ray tube and the receiver, and a support of the X-ray tube and receiver capable of displacing them along at least one axis, with a view to obtaining the positioning desired in relation to the organ to be studied. The radiology device further contains an electric power supply intended for the X-ray tube and possibly different electric motor or actuators, and a control of the X-ray tube making it possible to obtain the proper adjustments. The X-ray receiver is equipped with a digital type X-ray detector to display the image obtained on a video screen and/or to print it. U.S. Pat. No. 5,539,797 is an example of a known device.

When used the operator could commit errors resulting in serious disadvantages. For example, in the case of mammography, a lateral error can lead to taking a biopsy not on the breast presenting microcalcifications or other symptoms, but on the other breast with none of these symptoms.

BRIEF DESCRIPTION OF THE INVENTION

The present invention seeks to reduce the possibility of radiography errors.

The present invention seeks to automate the marking of an X-ray.

The present invention seeks to improve the quality of the images obtained.

The radiological imaging device, according to one aspect of the invention comprises means for emission of an X-ray beam and means for receiving the X-ray beam, after it has crossed an organ to be studied, and means for calculating capable of controlling the means for emission and processing data coming from the means for receiving, the organ being capable of being placed between the means for receiving and an element compressing the organ. The means for calculating comprises a means for optimizing the image quality on a particular area defined by the compression element.

The radiological imaging device, according to another aspect of the invention, is of the type comprises means for emission of an X-ray beam, means for receiving the X-ray beam after it has crossed an organ to be studied, an element presenting a given X-ray absorption capable of being removably fixed on the device, and a means for calculation for controlling the means for emission and of processing data from the means for receiving. The means for calculation include a means for optimizing the image quality over a particular area defined by the element.

The radiological imaging process, according to one aspect of the invention, includes the following stepes:

(a) an organ compression element is mounted on a radiological device, of the type including means for emission of an X-ray beam, means for receiving the X-ray beam after it has crossed an organ to be studied and means for calculating capable of controlling the means for emission and processing data coming from means for the receiving;

(b) the organ is placed between the means for receiving and the compression element, and a first radiological image is taken; and (c) the first radiological image is processed in order to optimize the image quality over a particular area defined by the compression element.

The radiological imaging process, according to another aspect of the invention, comprises the following steps:

(a) an element presenting a given X-ray absorption is placed on the path of an X-ray beam of a radiological device, the radiological device being of the type including means for emission of an X-ray beam, means for receiving the X-ray beam after it has crossed an organ to be studied and means for calculation capable of controlling the means for emission and processing data from the means for receiving;

(b) the organ is placed on the path of the X-ray beam, a first raiological image is taken, and (c) the first radiological image is processed in order to optimize the image quality on a particular area defined by the element.

The control program, according to one aspect of the invention, includes program code means for using the stage of the above-mentioned process.

The support, according to one aspect of the invention, is capable of being read by a device reading the program code means which are stored there and are suitable for use of the stages of the above-mentioned process.

DETAILED DESCRIPTION OF THE INVENTION

The invention is applicable in the medical field and, in particular, to an X-ray imaging device.

The device may include a means for recognition of the compression element.

The means for recognition may include at least one detection element and an adapter connected to an output of the detection element to transfer data from the detection element to a communication bus associated with the device. The detection element and the adapter can be formed on the same circuit, for example, integrated. The detection element can be of a mechanical type, such as a switch or magnetic, for example, a relay sensitive to magnetism or optical, for example, a photosensitive cell, etc.

In one embodiment of the invention, the means for calculation is capable of processing data from the means for recognition.

The device includes a coupling part of a compression element and the means for recognition may be placed in the coupling part.

The means for emission and the means for reception can be supported by an arm pivoting on at least one axis supported by a frame. The device can include a means for detecting the angle of pivoting of the arm, a means for entering data relating to the organ to be studied, a processing means capable of determining the type of image which is going to be taken as a function of the angle of pivoting and of the data relating to the organ, and a means for displaying on the image the type of image determined by the processing means or for storing the type of image determined with the image data, for example, in the heading of a computer file. The means for receiving may be capable of transforming the X-ray beam into a digital electronic signal.

The device can contain a menas for recognition of the compression element.

The compression element preferably includes a coder capable of cooperating with the means for recognition. The number of data that the coder can code will be equal to the number of data that the means for recognition can decode.

The compression element, according to one aspect of the invention, is capable of being removably fixed on a radiological imaging device, of the type including means for emission of an X-ray beam and means for receiving the X-ray beam after it has crossed an organ to be studied. The organ is capable of being placed between the means for receiving and the organ compression element. The compression element includes a coder capable of cooperating with a compression element means for recognition provided on a radiological imaging device.

The coder will be of the same type as the detection element: based on protuberances or hollows if the detection element is of mechanical type, based on magnets if the detection element is of magnetic type, based on light or dark surfaces if the detection element is of optical type, etc.

The compression element preferably includes a coupling part on a radiological imaging device, and the coder is integral with the coupling part.

The particular area is defined by the surface of the compression element in contact with the organ to be studied.

In one embodiment of the invention, optimization of the image quality is carried out from a histogram of the X-rayed image (real histogram), from a mathematical model of the image chain and from the object obtained by calibration.

(a) The mathematical model of the image chain and object and a set of parameters of acquisition, of the detector, of the positioner and of the object can be used to determine two gray level values, min_gray and max_gray, taken in the particular area and delimiting a useful gray level area, (b) The part below min_gray and the part above max_gray can be eliminated in the real histogram in order to obtain a limited histogram, (c) A set of rules can be applied to the limited histogram in order to determine a WL brightness level, (d) A WW contrast can be obtained from the WL brightness level and possibly from one or more parameters chosen by the user or fixed a priori.

The ($\mu$min) minimum linear attenuation coefficient of the object can be estimated from known values of the linear attenuation coefficient of the least attenuating tissues of the object (adipose tissues for the breast) for the energies of the X-ray spectrum determined by the acquisition parameters and makes it possible, with the parameter of the detector, the parameters of the positioner, the acquisition parameters and the parameters of the object, through a mathematical model of the image chain and object, to determine min_gray.

The ($\mu$max) maximum linear attenuation coefficient of the object can be estimated from known values of the linear attenuation coefficient of the most attenuating tissues of the object (fibrous tissues for the breast) for the energies of the X-ray spectrum determined by the acquisition parameters or, more precisely, from the mechanical thickness of the compressed breast, the acquisition parameters, the mathematical model of the image chain and the object and a quantity of photons obtained as a result of a pre-exposure made on an area of maximum density of the object, and makes it possible, with the parameters of the detector, the parameters of the positioner, the acquisition parameters and the object parameters, through a mathematical model of the image chain and object, to determine the min_gray gray level.

The limitation of the histogram can introduce two gray levels (min_gray and max_gray) encompassing an area of gray levels in which the WL brightness is determined.

A match can be made between the limited histogram and a mathematical model of the histogram in order to determine the value of a radiological thickness characterizing the object.

Matching between the limited histogram and mathematical model of the histogram can be carried out by applying a method of minimization of errors between two functions.

For the acquisition of a digital radiographic image of an object, an acquisition chain can contain a stage of equalization of the exponential attenuation effect of radiation by using a modified logarithmic function, so that the perception of contrast of a given difference in thickness remains invariant regardless of the means of acquisition.

The brightness level and the contrast obtained from a medium attenuation coefficient of the image independent of the brightness level can act on a stage of visualization so that the signals coming out of the equalization stage (space of radiological thicknesses) are dimensioned in the space of real thicknesses.

More precisely, the control program can be designed for a calculation unit of a radiological imaging device of the type comprising an emitter of an X-ray beam, a receiver of the X-ray beam after it has crossed an organ to be studied, and a calculation unit capable of controlling the emitter and processing data from the receiver. The organ is capable of being placed between the receiver and an organ compression element. The compression element is capable of being removably fastened on the device. The program includes a module for processing of the data from the recognition unit in order to optimize the image quality on a particular zone defined by the compression element.

Figure 1:
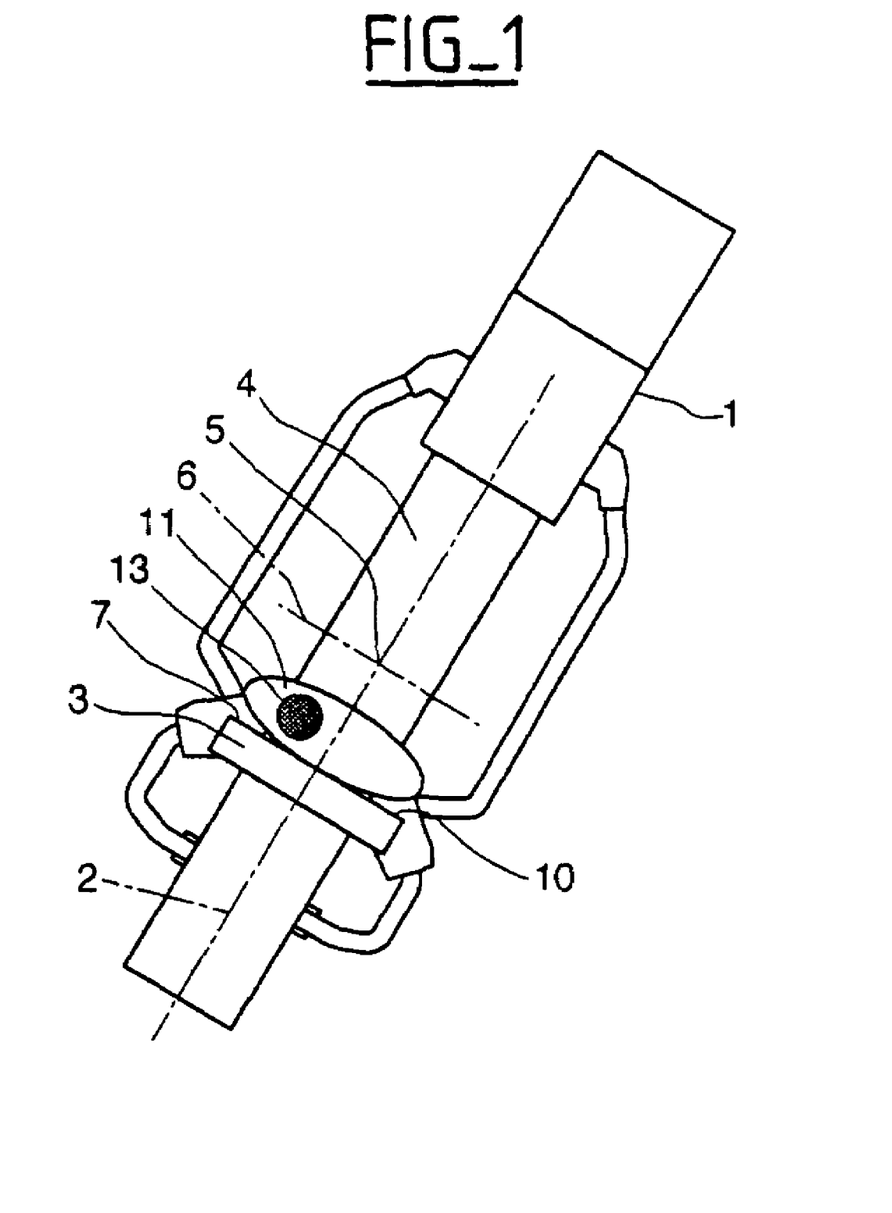
FIG. 1 is a view in perspective of a radiology device.

As can be seen in FIG. 1, the radiology apparatus comprises an X-ray tube 1 as a means for emission of an X-ray beam centered on an axis 2. On the path along which the X-rays are propagated and centered on axis 2, a receiver 3 is placed, as a means for receiving and transforming the incident X-rays into an electronic signal. The receiver 3 can be equipped with an X-ray detector of solid state type. The tube 1 and the receiver 3 are each supported at an opposite end of an arm 4 supported by a frame, not represented. The tube 1 and receiver 3 are mounted in rotating relation to the frame on an axis 5 perpendicular to the plane of the figure and passing through the intersection of axis 2 and the axis referenced 6, those three axes being perpendicular to each other. The arm 4, the tube 1 and the receiver 3 can be rotated on one complete turn in relation to the frame. The X-ray detector of the receiver 3 is equipped with a scanning system for reading the matrix of elementary detection cells constituting the detector.

In FIG. 1, a radiology apparatus with one axis is represented. Of course, this invention also applies to multiple-axis radiology apparatuses, for example, with C-arms with three axes or four axes.

The invention can be applied to a mammography apparatus using a screen-film pair (inside a cassette) as well as an apparatus using a digital detector. In the case of a film detector, the view name information will then be optically written on the film.

The use of compression ball or element information for control of exposure time as a function of the signal received on a pre-exposure is entirely possible. It is then necessary for the mammography apparatus to use a system composed of several cells (a cell matrix, for example) to measure the quantity of X-rays reaching different places of the detector during pre-exposure. The cell located under the compression ball and corresponding to the radiologically densest area of the object studied is typically chosen. A combination of the signal coming from several cells is also possible according to the average, the median value, etc. The method previously described chooses the maximum as algorithm.

Figure 2:
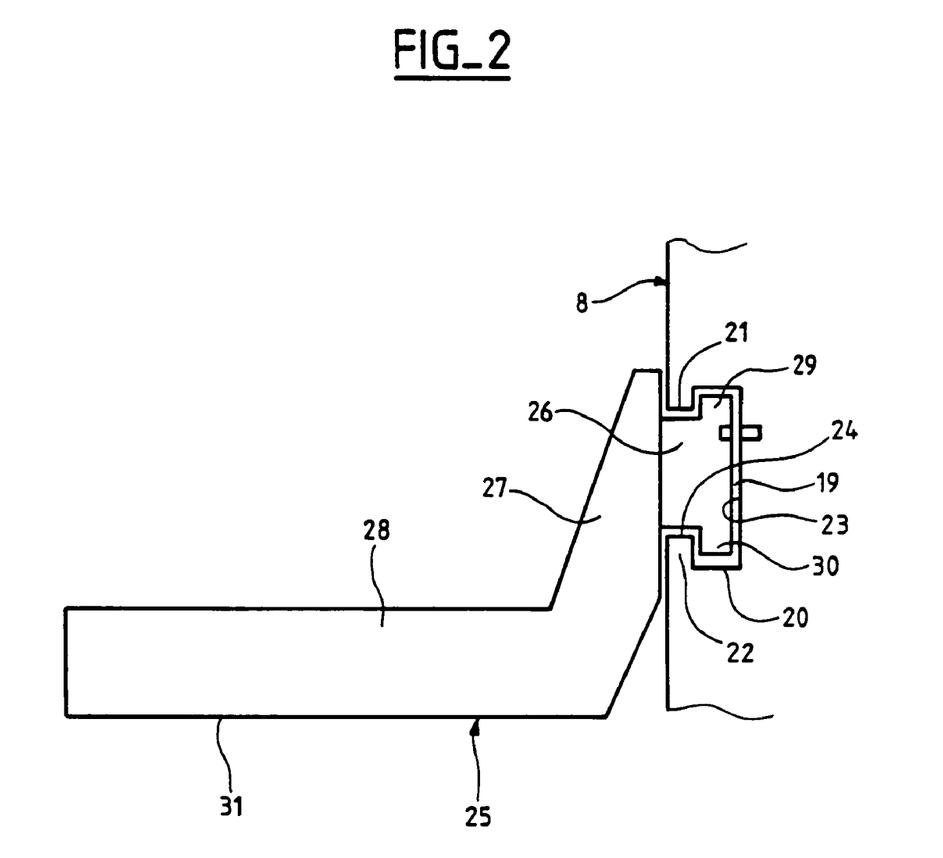
FIG. 2 is a partial side view showing the cooperation of a compression element and a radiology device.

In FIG. 2, a slightly different embodiment is illustrated, in which the column 8 of the radiology device 1 contains a horizontal slide 19 formed by a groove 20 limited by an upper edge 21 and a lower edge 22, so that the bottom 23 of the groove 20 presents a greater height than its opening 24.

A compression element or ball 25 is capable of cooperating with the slide 19 and contains a coupling part 26, a link part 27 and a contact part 28. The coupling part 26 is of a shape conforming to the slide 19 so that it can be placed inside. The coupling part 26 presents a rectangular section completed by two protuberances, upper 29 and lower 30, designed to be accommodated in the bottom 23 of the groove 20. The distance between the opposite ends of the protuberances 29 and 30 is greater than the distance between the opposite ends of the upper edge 21 and lower edge 22. The link part 27 extends from the coupling part 26 to the outlet of the groove 20 and supports the contact part 28, which presents a flat lower surface 31 capable of coming in contact with an organ, for example, the breast of a patient benefiting from a mammography examination. The contact part 28 can be made of material with low X-ray absorption, such as the material having the trade name Plexiglas, for example.

The compression element 25 can glide horizontally in the slide 19 and is removable from the column 8. For one and the same radiology device, different compression elements are generally used, of which only the coupling part 26 is similar for coupling in the slide 19. A means, not represented, for locking the translation movement in the slide 19 can be provided. To recognize the different compression elements, a coder 32 is fastened in or on the coupling part 26 of each compression element normally intended to be used with a corresponding radiology device. The coder can be of mechanical type in the form of keys, optical in the form of light or dark areas, or magnetic in the form of magnets. Here, the coder 32 contains a plurality of magnets, for example, four or five, cropping out of the surface of the coupling part 26 on the side of the bottom 23 of the groove 19.

The column 8 of the radiology device is equipped with a detection element 33 of the same technology as the coder. Here, the detection element 33 is capable of detecting a magnetic field emitted by the coder 32 and can contain a plurality of Hall-effect sensors or "reed" type magnetic relays in equal number to the number of magnets of the coder 32.

Figure 3:
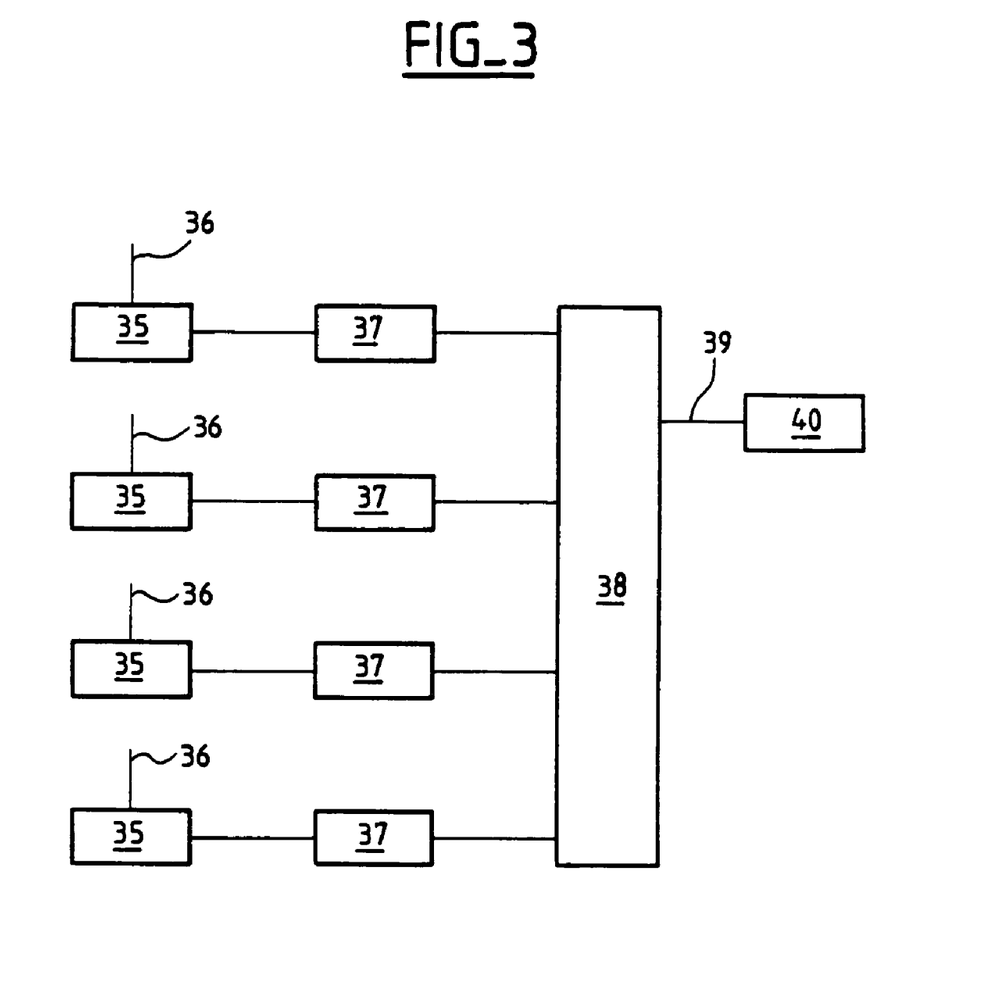
FIG. 3 is a schematic view of means for recognition.

The radiology device 1 can be equipped with a detection unit 34, as illustrated in FIG. 3. The detection unit 34 contains four relays 35 belonging to a detection element 33. Each relay 35 is fed through a line 36 with weak low-voltage electric power.

An adapter 37 receives a signal from a relay 35 and renders the signal compatible, notably, in voltage and output impedance, with the standard used for the electronics of the radiology device 1, for example, HCMOS. The adapters 37 can be separate or grouped, for example, on an integrated circuit.

The detection unit 34 further contains a serial converter 38 to permit communication by means of a data transfer bus 39, for example, RS 232, to a means for calculation unit 40 belonging to the radiology device 1. The calculation unit 40 may carry out image processing and will be equipped with memory and software for that purpose.

Figure 4:
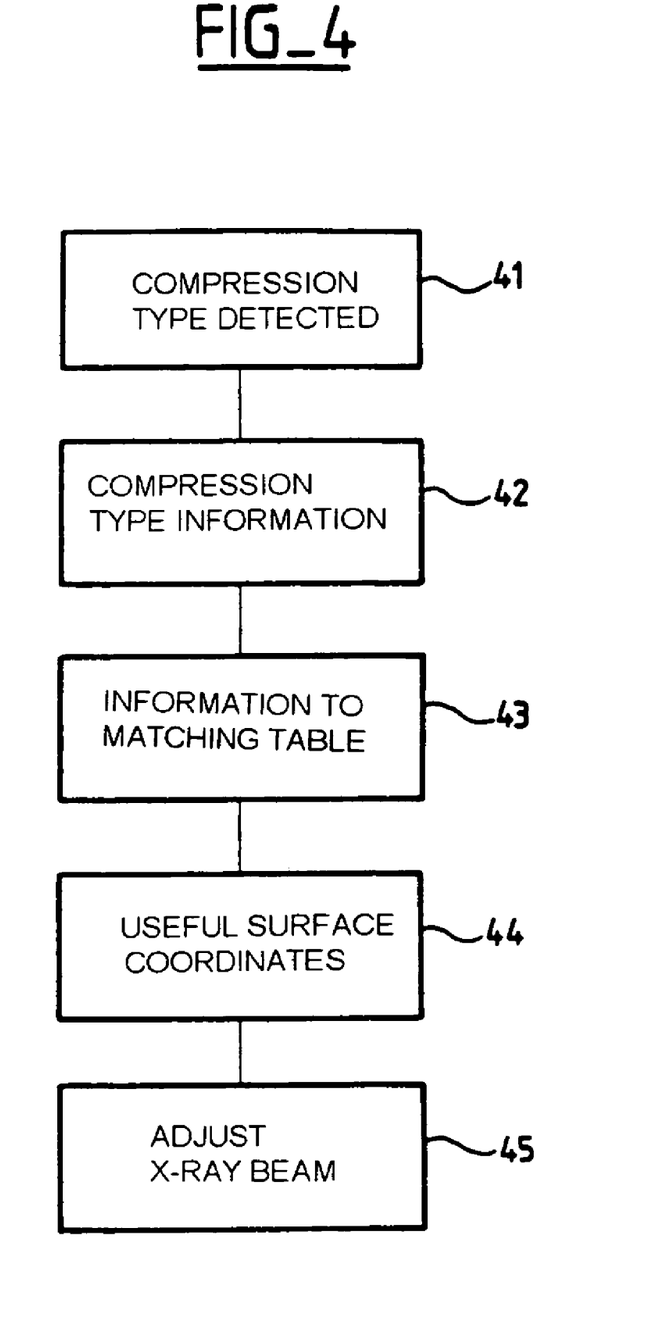
FIG. 4 is a diagrams of the steps of the process.
Figure 5:
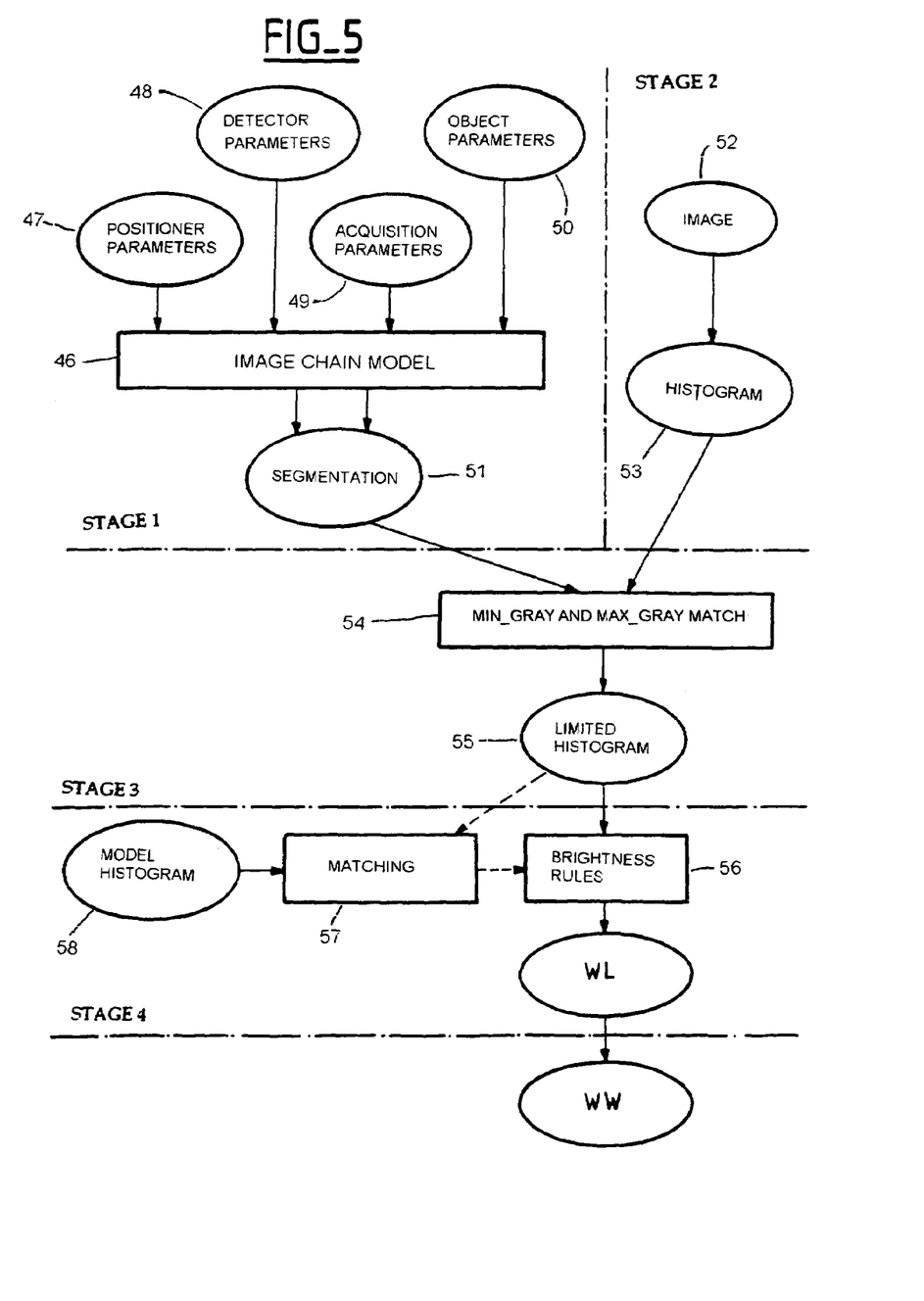
FIG. 5 is a flow chart of a method of use of the process.

The radiology device 1 can be operated as illustrated by FIG. 4. In stage 41, the radiology device 1 detects the type of compression element 25 placed in the slide 19 of the column 8, detection being carried out by the detection unit 34. In stage 42, the calculation unit 40 receives the "compression_element_type" information from the detection unit 34. In stage 43, the calculation unit 40 sends the "compression_element_type" information to a matching table stored in memory and receives from the table, in stage 44, "useful_surface_coordinates" information relating to the surface for which it is of interest to optimize the image quality. That surface can be the flat lower surface 31 of the contact part 28 of the compression element 25. In stage 45, the calculation unit 40 sends a command to the X-ray source 7 and, in particular, to a collimator, not represented, forming part of the source 7, to adjust the X-ray beam to the useful surface; in other words, for the area of the organ exposed to X-rays to match the useful surface, in order to reduce the total X-ray dose received by the patient.

The optimization can be achieved as follows: application of the process to the automatic determination of WL brightness and WW contrast is described in the particular case of mammography.

The first stage uses a mathematical model 46 of the image chain and of the object with the following parameters in input data:

(a) thickness of the compressed breast and parameters of the positioner (incidence of filming, enlargement factor, particular area defined by the compression element used, thickness of the object, compression force, etc.) as parameters 47 of the positioner, (b) parameters 48 of the detector (ratio between the X-ray flow received on the detector and the gray levels of the image produced, etc.), (c) acquisition parameters 49 (track, filter, kV, mAs, etc.), (d) object parameters 50 (mechanical thickness of the breast, $\mu_{min}$ minimum and $\mu_{max}$ maximum values of the linear attenuation coefficient of the object, etc.).

The breast consisting mainly of fibrous and adipose tissues, if there is no information on the composition of the breast, $\mu_{min}$ and $\mu_{max}$ can be estimated by making two extreme suppositions:

$\mu_{min}$ corresponds to the linear attenuation coefficient of the least attenuating tissues of the object (adipose tissues for the breast) inside the particular area defined by the compression element for the energies of the X-ray spectrum determined by the acquisition parameters;

$\mu$max can be estimated in two ways: on the one hand, like $\mu$min, by considering that $\mu$max corresponds to the linear attenuation coefficient of the most absorbent tissues of the object (fibers for the breast) inside the particular area defined by the compression element for the energies of the X-ray spectrum determined by the acquisition parameters. In another more precise way, from a mathematical model of the image chain, the mechanical thickness of the compressed breast, the acquisition parameters and a quantity of photons following a pre-exposure made on an area of maximum density (which makes it possible to estimate the value of the linear attenuation coefficient corresponding to the most attenuating area of the object).

Figure 6:
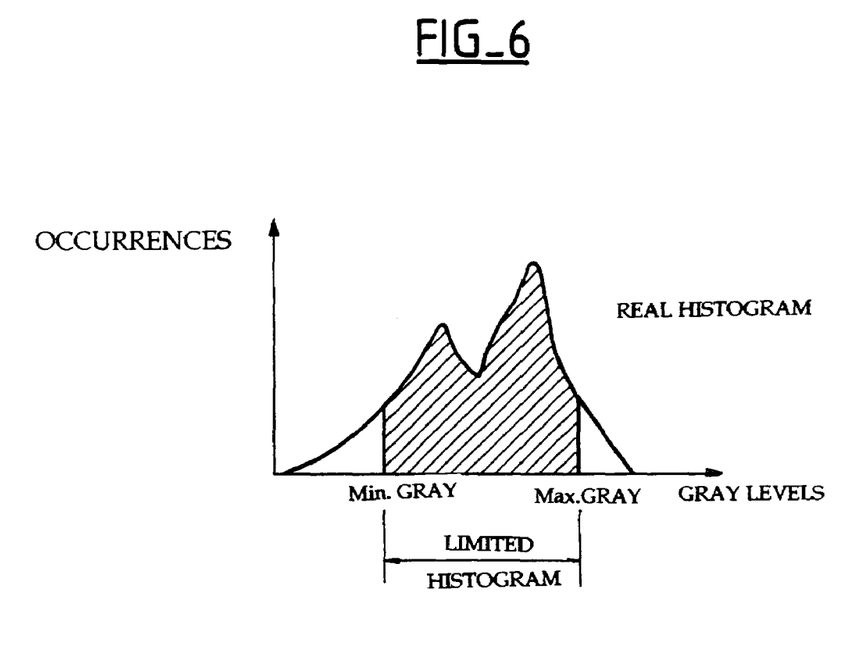
FIG. 6 is a curve showing the limited histogram in relation to the real histogram.

The set of parameters introduced in the mathematical model 46 of the image chain and of the object makes it possible to have two gray level values on output: min_gray and max_gray (FIG. 6). Those two values, in fact, delimit the useful area, which is an area of gray levels really pertaining to the breast. In fact, thanks to the two extreme values of the composition of the breast, $\mu$min and $\mu$max, an area delimited by two extreme values, min_gray and max_gray, was obtained, outside of which the gray levels do not correspond to the breast. More precisely, the part of the gray levels below min_gray corresponds to objects more attenuating than the object of interest, and the part of the gray levels above max_gray corresponds to the bottom of the image. Inside the particular area defined by the compression element, the useful area is determined. That stage 51 is a segmentation stage, for it makes it possible to delimit the useful area.

A match is then made (stage 54) between the two min_gray and max_gray values and a histogram 53 taken from the radiographic image 52 of the breast (real histogram). More precisely, the part below min_gray and the part above max_gray are eliminated so that the useful area is alone preserved in order to obtain a limited histogram 55 (FIG. 6).

Figure 7:
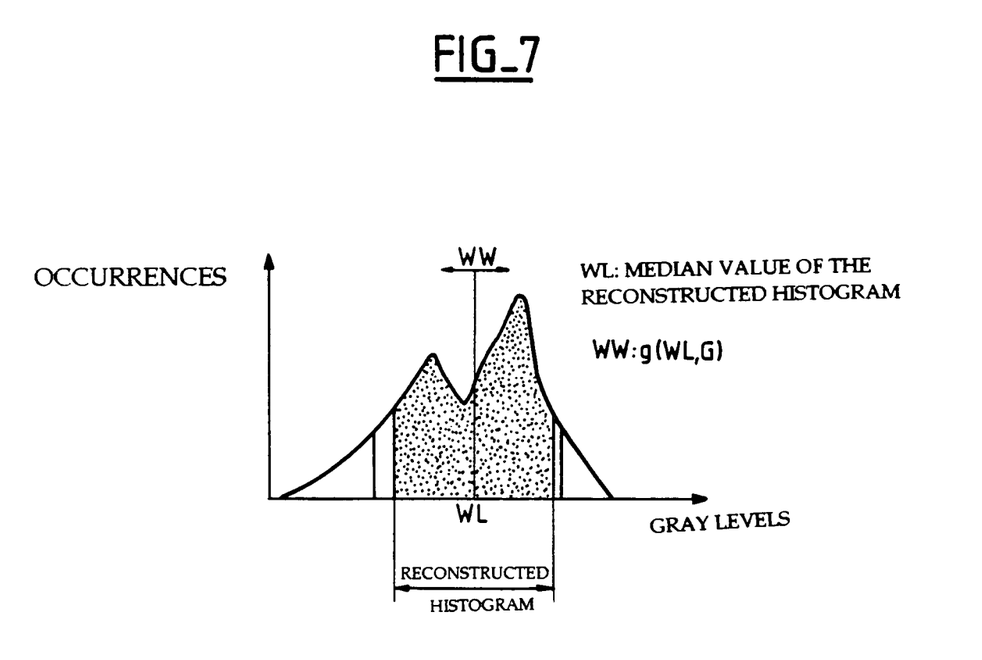
FIG. 7 is a curve showing a way of choosing WL.

The WL brightness is a value included in the useful area and can be obtained in several ways. One way of obtaining the WL brightness is application of a set of pre-established rules 56 to the limited histogram 55. A set of rules 56 can include:

(a) determination of the gray level corresponding to the maximum of the limited histogram;

(b) conservation of an x % quantity (typically 95%) of the occurrences of the histogram limited to the right of the maximum and also x % of the occurrences to the left of the maximum: a reconstructed histogram is thus obtained;

(c) determination of the WL brightness as median value of the reconstructed histogram (FIG. 7).

It is also possible to obtain the WL brightness with better precision by having the set of rules stage preceded by a matching stage 57. That stage introduces a mathematical model 58 of the histogram in which:

(a) the shape of the breast is a cylinder generated by rotation on an axis, from a rectangle, one of the narrow sides of which is closed by a semicircle of diameter equal to the length of that narrow side;

(b) the composition of the breast is homogeneous, for example, 100% fat;

(c) a histogram is established, which corresponds to probability as a function of the radiological thickness of the breast;

(d) the maximum of the histogram obtained represents the maximum thickness of the breast which, multiplied by the attenuation coefficient, gives the maximum radiological thickness corresponding to the adipose tissue.

Matching of the two histograms (mathematical model 58 and limited histogram 55) makes it possible to determine on the limited histogram 55 the value of the maximum radiological thickness corresponding to the adipose tissue in the breast.

This therefore makes it possible to determine the radiological thickness values of the different components of the breast.

This matching is made by employing a method of minimization of errors between two functions like, for example, the least squares method.

An adequate set of rules can then be applied to determine the WL brightness. For example, WL=$\alpha$.E with E representing the radiological thickness value obtained from the mathematical model 58 of the histogram.

The following step corresponds to determination of the WW contrast by using the WL brightness. The WW contrast is obtained from a function introducing the WL brightness and possibly from other parameters, notably, a parameter G (FIG. 7), which is chosen by the user. The parameter G therefore renders this process adaptable to each user: WW=g (WL, G), g being a function which, from WL brightness and G, determines the WW contrast that therefore represents a gray level scale around WL brightness.

It is also possible to determine the WW contrast independent of the WL brightness.

First, $\mu$ medium is determined from the information drawn from the limited histogram. For example, one can take the $\mu$ corresponding to the median value of the limited histogram as $\mu$medium.

A law introducing a constant Cte is then used to deduce from it the WW contrast:

$$WW=Cte\mu(\text{spectrum})$$

That ratio is true in a monoenergetic case, but in general the WW contrast is a function of the spectrum.

$$WW=f(\text{spectrum})$$

The self-contrast operation is thus carried out, since the WL brightness and WW contrast are established.

Figure 8:
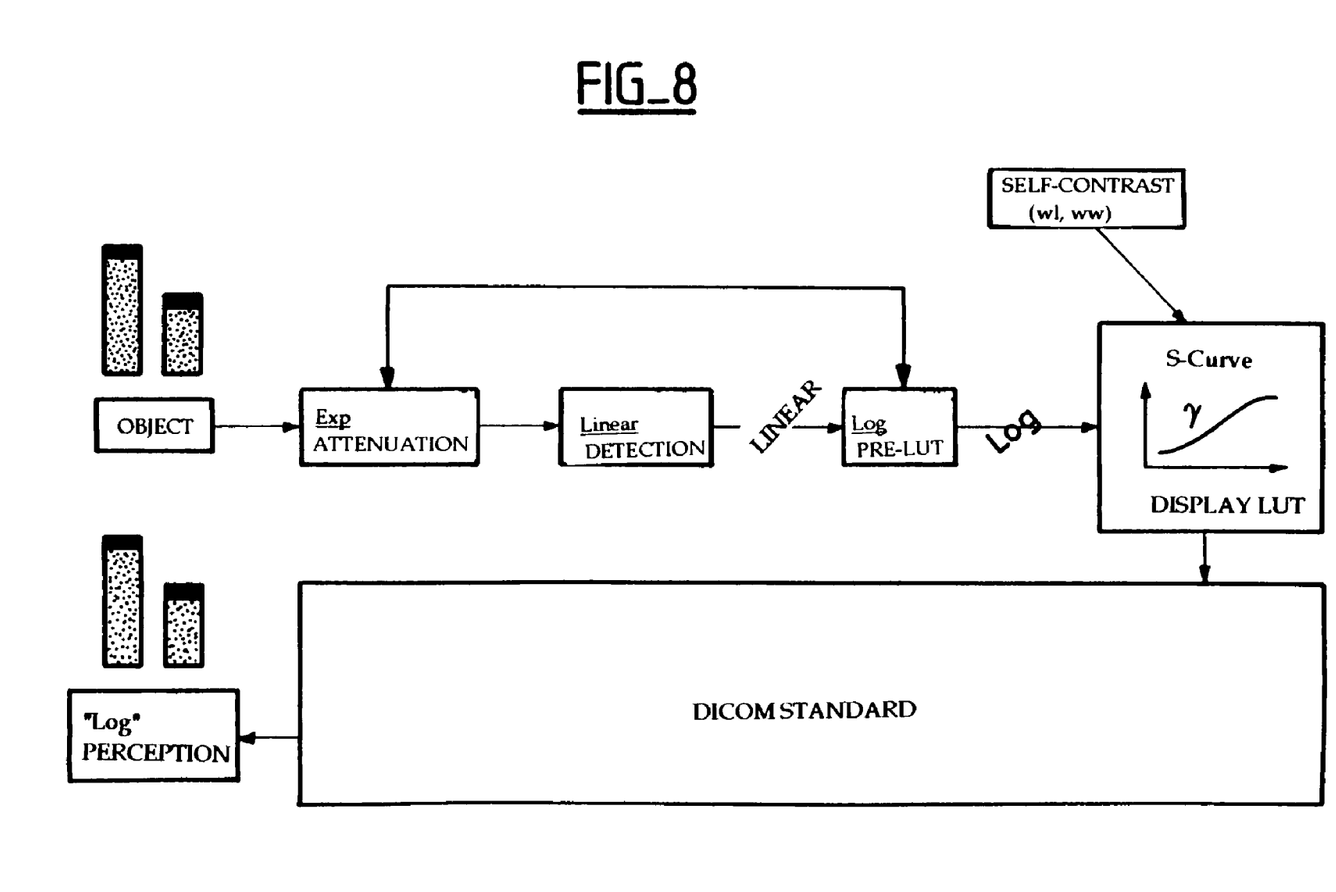
FIG. 8 is a diagram of the stages of the process of obtaining an invariant contrast.

What is now going to be described is the way in which the perception of contrast of a difference in thickness remains invariant, regardless of the means of acquisition and the objects, in accordance with FIG. 8.

The use of X-rays with the object entails an exponential attenuation of intensity I in the image:

$$I=I_o \exp(-\int \mu dl)$$

Io is a constant, dl represents an infinitesimal quantity corresponding to the distance along the path connecting the focus of the X-ray and the detector.

$\int dl$ represents the radiological thickness for a given area of an object.

In order to obtain that value, a pre-LUT (look-up table) operation is performed, making it possible to equalize the exponential attenuation by using a modified logarithmic function. It is the to be modified, for the lowest gray levels are transformed according to a linear function, while the logarithmic function progressively intervenes for the other gray levels.

One is thus in the space of radiological thicknesses in which a radiological thickness is noted $\mu$H with H the real thickness.

It is intended, finally, to make a change of space in order to be in the space of real thicknesses.

Self-contrast supplies us with the values of WW contrast and WL brightness that are introduced in a display LUT. The display LUT makes it possible to eliminate μ. In the case of a monoenergetic image, that operation comes down to a division by μ. This operation is possible, for the WW contrast is proportional to μ.

The result thus obtained can be introduced in the display system in order to display the image (FIG. 8).

The invention makes it possible, among other things, to improve the quality of the images displayed by a user, while reducing the X-ray dose.

The area on which the exposure is estimated from a pre-exposure can also be searched. It is then a question of determining, with a pre-exposure image obtained with a very low X-ray dose, what is the densest area of the part of the breast of interest to us in order to estimate the exposure time. Without a priori knowledge of the compression element used, the search of that area is carried out over the entire surface of the image. With a priori knowledge of the compression element used, and knowing the mechanical thickness of compression and the geometric enlargement factor used, a search area can be deduced therefrom on the pre-exposure image, limited to the useful part of the compression element used. This is particularly of interest for compression elements whose compression area is less than the sensitive surface area of the detector.

A possible optimization of exposure is thus avoided on an area outside the particular area defined by the compression element, which would have the effect of degrading exposure of the part of the breast under compression, which is the part of interest to the radiologist. The risk of an inadequate optimization is thus reduced.

Knowledge of the compression ball or element used makes it possible to control the X-ray collimator located at the outlet of the X-ray tube, for the purpose of limiting the irradiated area of the object studied.

When a compression ball or element of small surface is used, the collimator is adjusted, so that the X-rays can cross it, but also so that the X-rays cannot reach the parts of the object under compression whose entry surface would be outside the compression ball. Collimation can be chosen as a function of the shape or size of the compression ball, according to the size of the ball±N cm in each dimension, the table unequivocally connecting the compression ball used and the collimator opening, etc.

Various modifications in structure and/or steps and/or function may be made by one skilled in the art without departing from the scope of the invention.

What is claimed is:

1. A radiological imaging device, comprising:
   a. means for emission of an X-ray beam;
   b. means for receiving the X-ray beam after the beam has crossed an object to be studied; and
   c. means for calculation for controlling the means for emission and for processing data from the means for receiving;
   d. wherein the object is placed between the means for receiving and a means for compression;
   e. the means for compression being removably fixed on the device; and
   f. the means for calculation including means for optimizing image quality over a particular area defined by the means for compression.

2. The device according to claim 1, comprising: means for recognition of the means for compression.

3. The device according to claim 2, wherein the means for recognition includes at least one detection element and an adapter connected to an output of the detection element for transfer of data from the detection element to a communication bus associated with the device and the means for calculation for processing data from the means for recognition.

4. A radiological imaging device comprising;
   a. means for emission of an X-ray beam;
   b. means for receiving the X-ray beam after the beam has crossed an object to be studied;
   c. an element having a given X-ray absorption removably fixed on the device; and
   d. means for calculation for controlling the means for emission and for processing data from the means for receiving, the means for calculation including means for optimizing image quality over a particular area defined by the element.

5. The device according to claim 4, wherein the element includes means for coding for cooperating with a means for recognition of the element.

6. A radiological imaging method, in which a compression element for an object is mounted on a radiological device having means for emission of an X-ray beam and means for receiving the X-ray beam after the beam has crossed the object to be studied and means for calculation for controlling the means for emission and for processing data from the means for receiving, comprising the steps for:
   a. placing the object between the means for receiving and the compression element;
   b. taking a first radiological image of the object; and
   c. processing the first radiological image in order to optimize image quality over a particular area defined by the compression element.

7. The method according to claim 6, in which the particular area is defined by a surface of the compression element in contact with the object to be studied.

8. The method according to claim 6 comprising the steps for:
   a. establishing a histogram of the image (real histogram);
   b. establishing a mathematical model of an image chain;
   c. determining parameters of the object by calibration;
   d. determining parameters for acquisition of the image;
   e. determining parameters of the means for receiving;
   f. determining parameters for positioning the device;
   g. using steps a to f to determine two gray level values, min_gray and max_gray, taken in the particular area and delimiting a useful gray area;
   h. eliminating the part below $min_{13}$ gray and the part above $max_{13}$ gray in the real histogram in order to obtain a limited histogram;
   i. applying a set of rules to the limited histogram in order to determine a WL brightness level; and
   j. obtaining a WW contrast from the WL brightness level and possibly from one or more parameters chosen by a user or fixed a priori.

9. The method according to claim 7 comprising the steps for:
   a. establishing a histogram of the image (real histogram);
   b. establishing a mathematical model of an image chain;
   c. determining parameters of the object by calibration;
   d. determining parameters for acquisition of the image;
   e. determining parameters of the means for receiving;
   f. determining parameters for positioning the device;
   g. using steps a to f to determine two gray level values, min_gray and max_gray, taken in the particular area and delimiting a useful gray area;

h. eliminating the part below min_gray and the part above max_gray in the real histogram in order to obtain a limited histogram;
i. applying a set of rules to the limited histogram in order to determine a WL brightness level; and
j. obtaining a WW contrast from the WL brightness level and possibly from one or more parameters chosen by a user or fixed a priori.

10. A radiological imaging process, in which an element having a given X-ray absorption is placed in a path of an X-ray beam of a radiological device, the radiological device comprising means for emission of the X-ray beam and means for receiving the X-ray beam after the beam has crossed an object to be studied and means for calculation for controlling the means for emission and for processing data from the means for receiving, comprising the steps for:
   a. placing the object in the path of the X-ray beam;
   b. taking a first radiological image of the object and;
   c. processing the first radiological image in order to optimize image quality on a particular area defined by the element.

11. An article of manufacture comprising:
   a. a computer useable medium having computer readable program code means embodied therein for taking a first radiological image by a device having means for emission of an X-ray beam and means for receiving the X-ray beam after the beam has crossed an object to the studied, wherein the object is disposed between the means for emission and a means compression, and means for calculation for controlling the means for emission and means for processing data from the means for receiving; and
   b. the computer readable program code means processing the first radiological image for optimizing the image quality over a particular area defined by the means for compression.

12. The article of claim 11 wherein the computer readable program code means comprises program code for causing a coder for the means for compression to cooperate with means for recognition of the means for compression.

13. The article of claim 11 wherein the computer readable program code means comprises steps for:
   a. forming a real histogram of the image;
   b. establishing a mathematical model of an image chain;
   c. determining parameters of the object by calculation;
   d. determining parameters for an acquisition of the image;
   e. determining parameters of the means for receiving;
   f. determining parameters for positioning of the device;
   g. determining two gray levels values, min_gray and max_gray, taken in a particular area and delimiting a gray area;
   h. eliminating a part below min_gray and a part above max_gray in the histogram in order to obtain a limited histogram;
   applying a set of rules to the limited histogram in order to determine a WL brightness level; and
   j. obtaining a WW contrast from the WL brightness level and possible from one or more parameters chosen by the user or fixed a priori.

14. The article of claim 11 wherein the article is a support capable of being read by a reading device for the computer readable program code means embodied therein.

15. A program storage device readable by a machine, tangibly embodying a program of instructions executable by the machine to perform method steps for taking a radiological image of an object, the method steps comprising:
   a. forming a real histogram of the image;
   b. establishing a mathematical model of an image chain;
   c. determining parameters of the object by calculation;
   d. determining parameters for an acquisition of the image;
   e. determining parameters of a means for receiving;
   f. determining parameters for positioning of the device;
   g. determining two gray levels values, min_gray and max_gray, taken in a particular area and delimiting a gray area;
   h. eliminating a part below min_gray and a part above max_gray in the histogram in order to obtain a limited histogram;
   i. applying a set of rules to the limited histogram in order to determine a WL brightness level; and
   h. obtaining a WW contrast from the WL brightness level and possible from one or more parameters chosen by the user or fixed a priori.

* * * * *

UNITED STATES PATENT AND TRADEMARK OFFICE
CERTIFICATE OF CORRECTION

PATENT NO. : 7,133,490 B2  
APPLICATION NO. : 09/825910  
DATED : November 7, 2006  
INVENTOR(S) : Serge Muller et al.

Page 1 of 1

It is certified that error appears in the above-identified patent and that said Letters Patent is hereby corrected as shown below:

Column 1:  
Line 51, after "and", insert --a--.  
Line 60, after "type", insert --that--.

Column 2:  
Line 46, after "a", delete "diagrams" and insert therefor --diagram--.

Column 3:  
Line 22, after "a", delete "menas" and insert therefor --means--.

Column 5:  
Line 64, after "23 of the groove", delete "19" and insert therefor --20--.

Column 10:  
Line 48, after "below", delete "min$_{13}$" and insert therefor --min_--.  
Line 49, after "above", delete "max$_{13}$" and insert therefor --max_--.

Column 11:  
Line 27, after "to", delete "the" and insert therefor --be--.  
Line 29, before "compression", insert --for--.  
Line 33, after "means", insert --for--.

Column 12:  
Line 7, after "gray", delete "levels" and insert therefor --level--.

Signed and Sealed this

Seventh Day of August, 2007

JON W. DUDAS  
*Director of the United States Patent and Trademark Office*